(12) United States Patent
Bromley-Davenport et al.

(10) Patent No.: US 8,877,336 B2
(45) Date of Patent: Nov. 4, 2014

(54) MEDICAMENT DISPENSER DEVICE

(75) Inventors: Darren Bromley-Davenport, Marton (GB); Paul Stevenson, Little Weighton (GB)

(73) Assignee: Portal Medical Ltd., Chester (GB)

( * ) Notice: Subject to any disclaimer, the term of this patent is extended or adjusted under 35 U.S.C. 154(b) by 0 days.

(21) Appl. No.: 13/580,956

(22) PCT Filed: Feb. 23, 2011

(86) PCT No.: PCT/GB2011/050350
§ 371 (c)(1),
(2), (4) Date: Oct. 17, 2012

(87) PCT Pub. No.: WO2011/104539
PCT Pub. Date: Sep. 1, 2011

(65) Prior Publication Data
US 2013/0025592 A1    Jan. 31, 2013

(30) Foreign Application Priority Data

Feb. 26, 2010    (GB) .................................. 1003273.8

(51) Int. Cl.
| | | |
|---|---|---|
| *B32B 7/12* | (2006.01) | |
| *A61M 15/00* | (2006.01) | |
| *B05D 1/00* | (2006.01) | |
| B05D 5/08 | (2006.01) | |
| B05D 7/22 | (2006.01) | |

(52) U.S. Cl.
CPC ..... *A61M 15/009* (2013.01); *A61M 2205/0238* (2013.01); *B05D 5/083* (2013.01); *B05D 2202/00* (2013.01); *B05D 7/227* (2013.01); *A61M 2207/00* (2013.01); *B05D 1/62* (2013.01)
USPC ...................... 428/344; 428/35.8; 128/203.12

(58) Field of Classification Search
CPC .................. A61M 15/009; A61M 2205/0238; A61M 2207/00; B05D 1/62; B05D 5/083; B05D 7/227; B05D 2202/00
USPC .............................. 428/35.8, 344; 128/203.12
See application file for complete search history.

(56) References Cited

U.S. PATENT DOCUMENTS

| | | | |
|---|---|---|---|
| 8,430,097 B2 * | 4/2013 | Jinks et al. ............... | 128/203.12 |
| 2003/0031806 A1 | 2/2003 | Jinks | |
| 2006/0068224 A1 | 3/2006 | Grobe et al. | |
| 2013/0025592 A1 * | 1/2013 | Bromley-Davenport et al. ........................ | 128/203.12 |

FOREIGN PATENT DOCUMENTS

| | | |
|---|---|---|
| EP | 0642992 A2 | 3/1995 |
| EP | 1066073 B1 | 6/2002 |
| JP | 2004277800 A | 10/2004 |
| WO | 03024623 A1 | 3/2003 |

(Continued)

OTHER PUBLICATIONS

ISA European Patent Office, Search Report of PCT/GB2011/050350, Jul. 21, 2011, Netherlands, 10 pages.

*Primary Examiner* — N. Edwards
(74) *Attorney, Agent, or Firm* — Alleman Hall McCoy Russell & Tuttle LLP

(57) ABSTRACT

According to the invention there is provided a dispenser device for dispensing a medicament, the device including at least one metallic component having at least one non-metallic surface which comes into contact with the medicament during storage or use of the device, in which said non-metallic surface has an interface with the underlying metallic component which substantially comprises metal-fluoride and/or metal-carbide moieties.

12 Claims, 2 Drawing Sheets

(56) References Cited

FOREIGN PATENT DOCUMENTS

| WO | 03035154 A1 | 5/2003 |
| WO | 2008146024 A2 | 12/2008 |
| WO | 2008146025 A2 | 12/2008 |
| WO | WO2009/061891 * | 5/2009 |

* cited by examiner

MEDICAMENT DISPENSER DEVICE

CROSS REFERENCE TO RELATED APPLICATIONS

The present application is the U.S. national phase pf PCT/GB2011/050350 filed Feb. 23, 2010, which claims priority to GB Application No. 1003273.8 filed Feb. 26, 2010, the entire disclosures of eeach of which are hereby incorporated by reference.

This invention relates to dispenser devices for dispensing a medicament, methods of manufacturing same and methods of treating a component of same, with particular, but by no means exclusive, reference to pressurised dispenser devices.

It is well known to administer medicaments to a patient by inhalation using pressurised dispenser devices which dispense the medicament in a carrier fluid. The medicament may be present as a particulate suspension or in solution or even as a combination of the two. Such devices are often referred to as pressurised metered dose inhalers (pMDIs), and are very commonly used for treating asthma and chronic obstructive pulmonary disease (COPD).

Problems associated with dispenser devices of this kind include absorption, binding or degradation of the active medicament on the internal surfaces of the device, and corrosion of the delivery device components by the medicament itself. This in turn can lead to a loss of potency and/or erratic dosing during the shelf-life of the device. In some instances clustering of drug particles can occur if the active medicament is present as a suspension of particles. One approach that has been adopted in order to reduce the surface absorption of the active drug is to deposit a low energy polymer or inorganic coating (or combination of the two) by plasma deposition. EP 0642992, EP1066073 and WO 2008/146024 are examples of prior art documents which disclose plasma polymerisation onto various components of the dispenser devices. However, it is recognised that a number of delivery problems can exist with coatings of this type. One problem pertains to devices which use a particulate suspension as the delivery system. These delivery systems can be affected by adherence of the medicament particles to and "caking" of these particulates on the walls of the can or on other surfaces within the dispenser device. This may lead to agglomerations which affect the medicament dose. A second problem is due to autocatalytic degradation of some medicaments through contact with certain materials, in particular metal oxides such as aluminium oxide and magnesium oxide, and other reactions between the components and medicaments such as corrosion. Certain components of dispenser devices, in particular the can body, are formed from aluminium, and consequently have an aluminium oxide surface layer which also contains alloying compounds such as magnesium oxide. Coating such components with a barrier potentially provides a way in which both degradation and, with a non-stick barrier, the adherence of medicament particles to surfaces might be prevented. However, it is not always necessary to have non-stick properties if degradation and/or corrosion are the only concern with a particular drug (for example, if the drug is present in a solution delivery system). Additionally, the performance of some coatings can be less than optimal for various reasons. One such reason is that coatings may have flaws or pinholes present which enables medicament molecules present in a solution to reach the surface of the component parts such as the aluminium oxide surface of a can, where degradation and/or corrosion can take place.

The present invention, in at least some of its embodiments, addresses the above described problems and needs.

According to a first aspect of the invention there is provided a dispenser device for dispensing a medicament, the device including at least one metallic component having at least one non-metallic surface which comes into contact with the medicament during storage or use of the device, in which said non-metallic surface has an interface with the underlying metallic component which substantially comprises metal-fluoride and/or metal carbide moieties.

The present invention provides a surface modification of the surface of one or more metallic components of a dispenser device. The surface modified interface substantially eliminates or at least reduces degradation of medicaments which are susceptible to such processes in comparison to the otherwise untreated surface of the metallic component. Susceptibility to corrosion can be significantly decreased.

In one embodiment, the interface does not have a coating deposited thereon. In these embodiments, it is the interface itself which comes into contact with the medicament during storage or use of the device. In such embodiments, the non-metallic surface consists of essentially the interface so that the interface comes into contact with the medicament during storage or use of the device. The metal-fluoride and metal carbide moieties are extremely stable, and can provide a surface which does not degrade many drug formulations and provides corrosion inhibition. Embodiments in which the interface substantially comprises metal-fluoride moieties are particularly preferred for these applications.

In other embodiments, the non-metallic surface includes a coating which is deposited on the interface so that the coating comes into contact with the medicament during storage or use of the device. The coating may be a polymer coating or an inorganic coating. Preferably, the coating is a plasma polymerised polymer coating. It has been found that the surface modified interface can provide an excellent substrate for the subsequent deposition of a plasma polymerised coating. However, it is possible to employ one or more further surface treatments or preparations prior to depositing the coating, ie, in addition to embodiments in which the interface is directly coated with the coating, the invention includes embodiments in which the interface is indirectly coated with the coating. Furthermore, the surface modified interface can protect against degradation of many drug formulations and corrosion if there are flaws present in the coating (however deposited) which would otherwise allow the drug formulation access to an uncoated portion of the surface of the metallic component.

In embodiments in which the interface substantially comprises metal-fluoride moieties, the polymer coating may be a fluorocarbon polymer, preferably a per-fluorocarbon polymer.

In embodiments in which the interface substantially comprises metal-carbide moieties, the polymer coating is preferably a hydrocarbon polymer but could also be a fluoropolymer or a combination of the two.

Advantageously, the interface comprises less than about 15 At %, preferably less than about 10 At %, more preferably less than about 7 At % oxygen as measured by X-Ray Photoelectron Spectroscopy (XPS). Most preferably, the interface comprises about 5% or less At % oxygen as measured by XPS. Generally, the At % should be as close to zero as the process and grade of metal used permits. In this way, the possibility of degradation of the medicament is minimised and corrosion performance maximised.

Advantageously, the interface comprises less than about 25 At %, preferably less than about 5 At %, more preferably less than about 1 At % metal ions as measured by X-Ray Photo-electron Spectroscopy (XPS). Without wishing to be bound by any particular theory or conjecture, it is believed that unreacted metal ions at the interface can be responsible for degradation of the medicament. Also, it is believed that the surface modification provided by the invention reduces the number of unreacted metal ions at the interface.

The dispenser device may be in the form of a pressurised dispenser device which dispenses the medicament in a carrier fluid.

Preferably, the dispenser device includes a metallic can body. However, other components of the dispenser devices, such as valve stems and springs, may be surface modified in accordance with the invention.

Advantageously, the metallic component is formed from aluminium but the invention is not limited to aluminium and the formation of carbides and fluorides of other metals are possible. In particularly preferred embodiments, the metallic component is an aluminium can body. Alternatively, the metallic component may be formed from stainless steel.

According to a second aspect of the invention there is provided a metallic component for a dispenser device that dispenses a medicament, the component having at least one non-metallic surface which comes into contact with the medicament during storage or use of the device, in which said non-metallic surfaces has an interface with the underlying metallic component which substantially comprises metal-fluoride and/or metal carbide moieties.

The metallic component may be in the form of a metallic can body for use in a pressurised dispenser that dispenses the medicament in a carrier fluid, in which the non-metallic surface is an interior surface of the can body.

According to a third aspect of the invention there is provided a method of treating a metallic component of a medicament dispenser device, the component having at least one non-metallic surface which comes into contact with the medicament during storage or use of the device, the method including steps of:

providing said components; and surface modifying said non-metallic surface in a plasma treatment step using a fluorine and/or carbon containing precursor under conditions including a substantial absence of oxygen which lead to the formation of an interface with the underlying metallic component, wherein the interface substantially comprises metal-fluoride and/or metal carbide moieties.

The metallic component which has been surface modified in this way may then be used directly in a medicament dispenser device, i.e. the surface modified interface may come into contact with the medicament during storage or use of the device.

In alternative embodiments, the method further includes the step of depositing a coating onto the interface so that the coating comes into contact with the medicament during storage or use of the device. The coating may be deposited by plasma deposition.

Preferably, the coating is a polymer coating. Advantageously, the polymer coating is deposited by plasma polymerisation.

The coating may be an inorganic coating, which may be deposited by plasma deposition.

In embodiments in which the interface substantially comprises metal-fluoride moieties, the precursor may be a fluorocarbon, preferably a per-fluorocarbon. The per-fluorocarbon may be of the formula $CnF2n+2$ where n is in the range of 1 to 8. In general, smaller precursors are preferred, because the proportion of fluorine is greater. Cyclic and/or unsaturated per-fluorocarbons may be used. Particularly preferred precursors are $CF4$ and cyclic $C4F8$. Other suitable precursors include $C2F6$, $C3F8$, $C5F10$ and the chemicals HFA134a (1,1,1,2,-tetrafluoroethane) and HFA227 (1,1,1,2,3,3,3-heptafluoropropane) which are commonly used as propellants in medicament dispenser devices.

In embodiments in which the interface substantially comprises metal-carbide moieties, the precursor may be a hydrocarbon, preferably methane or ethane, $C3H8$ and $C4H10$ are also preferred. In general, alkanes of the formula $CnH2n+2$ where n is 1 to 12 can be used. Alkenes and alkynes may be used. Cyclic hydrocarbons may be used as the precursor.

Advantageously, at least part of the plasma treatment step is performed under DC bias control or using a minimum DC bias. The entire plasma treatment step may be performed under DC bias control or, alternatively, DC bias control may be employed at a desired point after commencement of the plasma treatment step.

Typically, if DC bias control is not employed, then the plasma treatment step is implemented using forward power mode with a minimum DC bias.

The bombardment energy of incoming ions created in the plasma is proportional to the DC bias voltage. Preferably, the DC bias control is performed using a DC bias voltage in the range of 100 to 800 volts, preferably in the range of 350 to 700 volts, most preferably in the range of 400 to 550 volts. With these DC biases, the level of ion bombardment is significant, and fluorine ions are significantly accelerated so as to become embedded in the surface without any surface polymerisation. Undesirable species present on the surface such as carbon, native oxides and other deleterious material can be sputtered away. Advantageous, the DC bias voltage is greater than or equal to 350 volts, preferably 500 volts. In embodiments (such as operation in forward power mode) in which a minimum DC bias is employed, the minimum DC bias adopted may be in the ranges indicated above in connection with the DC bias voltage used under DC bias control.

In certain preferred embodiments, the plasma treatment step is performed by applying an RF potential to the component. In this way, in hollow components, a "hollow cathode" effect can be created which is advantageous since electrons emitted at the RF potential of the component cannot easily escape. The effect can be a plasma which is significantly more energetic than the volume away from the component. This effect is particularly pronounced when the component is a can, wherein the electrons emitted in the can interior at the RF potential of the can cannot escape from the can interior. Under these conditions, the surface may be surprisingly heavily bombarded with reactive fluorine using surprisingly low power levels, thereby providing an efficient process. For components that are not hollow and cannot utilise this effect, placing them at RF potential provides better surface bombardment due to ion acceleration in the plasma sheath created at the surface to be treated.

Alternatively, the plasma treatment step may be performed by holding the component at earth. This approach is particularly preferred with embodiments in which a plasma deposited coating is subsequently produced, since the subsequent process of plasma coating is advantageously performed with the metallic component at earth, and therefore it is possible to perform the surface modification and the subsequent plasma deposition steps with minimal disruption to the apparatus used to treat the component.

Preferably, the plasma treatment step is performed using a power density in the range of 0.05 to 5 Wcm-2, preferably 0.1 to 1 Wcm-2.

The component may undergo a cleaning step prior to the step of surface modification. Preferably, the cleaning step utilises a plasma cleaning treatment, and most preferably a plasma is formed using argon. It is important that oxygen is excluded from any cleaning step, since oxygenation of the surface of the component can make the conversion of the surface to a fluoride or carbide more difficult. Additionally, any oxygen absorbed into the walls of the processing apparatus can leach out and disassociate any subsequently deposited plasma coating, making a subsequent plasma coating step more difficult and disadvantageous as well.

According to a fourth aspect of the invention there is provided a method of manufacturing a medicament dispenser device, the method including the steps of:

treating a component of the dispenser device in a method according to the third aspect of the invention; and assembling the components to provide an assembled medicament dispenser device.

Whilst the invention has been described above, it extends to any inventive combination as set out or in the following description, drawings or claims.

Embodiments of methods and dispenser devices in accordance with the invention will now be described with reference to the accompanying drawings, in which:

BRIEF DESCRIPTION OF THE DRAWINGS

FIG. 1 depicts a pressurised dispenser device, shown generally at 10, which comprises a housing 12 which receives a pressurised medicament containing arrangement 14. The housing 12 comprises an open ended cylindrical portion 12a in which the pressurised medicament containing arrangement 14 is disposed, and an open ended passage 12b which serves as a mouthpiece. The housing 12 further comprises an inner wall 12c which supports a socket 12d having a passageway 12e which receives the valve stem of the pressured medicament container arrangement. The passageway 12e communicates with an opening 12f which in turn is in communication with the exit passage defined by the open ended passage 12b. The inner wall 12c has a number of apertures 12g formed therein which permits air to flow from the upper area of the housing 12 into the open ended passage 12b.

Figure 1:
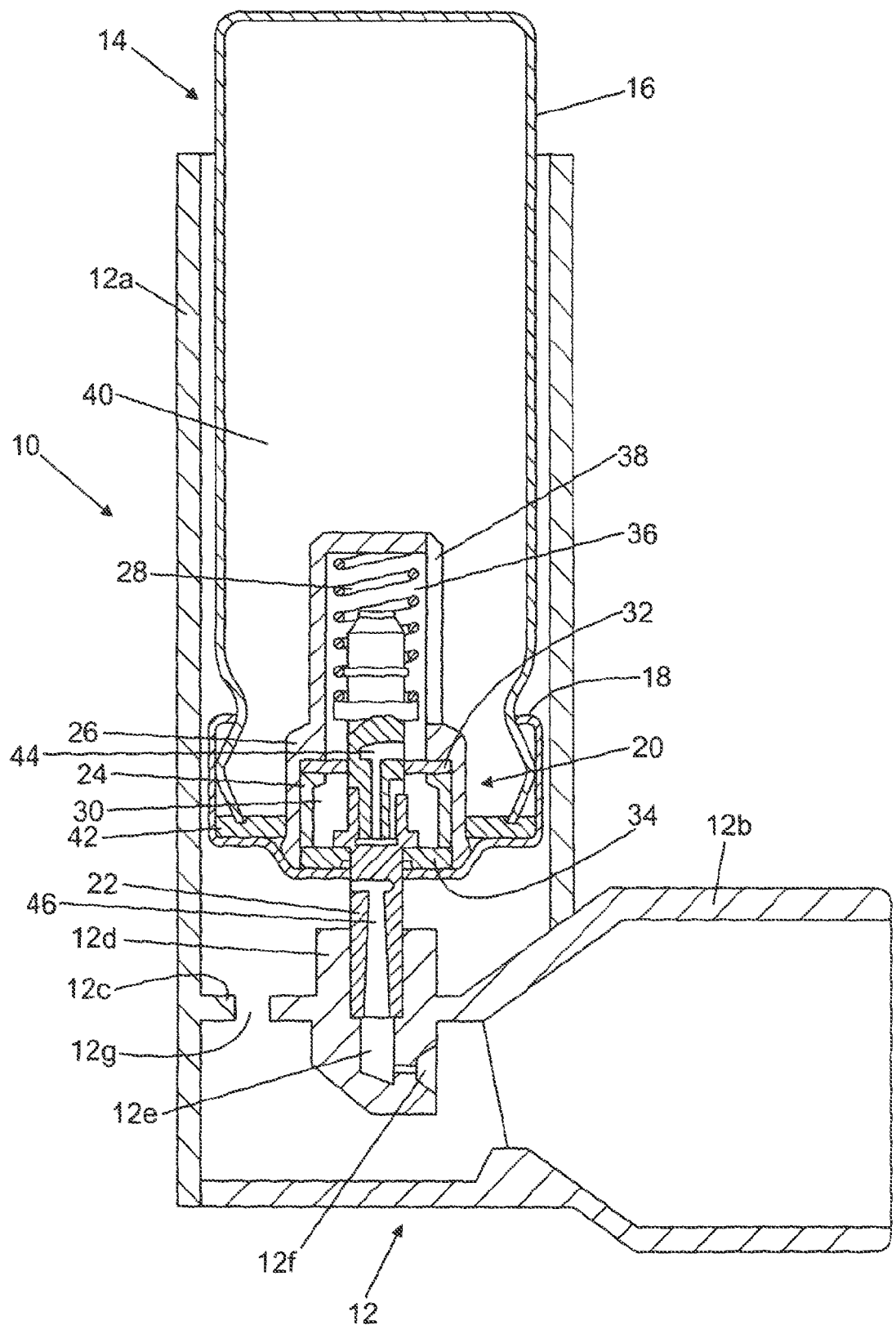
FIG. 1 is a cross sectional view of a pressurised dispenser device.

The structure and operation of the pressurised medicament container arrangement 14 will now be described in more detail. The arrangement 14 comprises a can body 16 on which is crimped a ferrule 18. Mounted on the ferrule 18 is a metering valve system, shown generally at 20. The metering valve system 20 comprises a valve stem 22, a portion of which is disposed in a valve member 24. The valve stem 22 and valve member 24 are both located in a valve housing 26, and the valve stem 22 is axially reciprocable therein against the action of a spring 28 which biases the valve stem 22 into a closed position as shown in FIG. 1.

The metering valve system 20 further comprises a metering chamber 30 which is defined by the valve member 24 and a portion of the valve stem 22 together with inner and outer seals 32, 34. The inner seal 32 acts to seal the valve member 24 against the valve housing 26, and separates the metering chamber 30 from the interior 36 of the valve housing 26. The outer seal 34 acts to seal the valve member 24 and valve housing 26 against the ferrule 18, and also seals the metering chamber 30 from the outside of the pressurised medicament container arrangement 14.

Further sealing is provided by a can body seal 42 which acts to seal the can body 16 against the ferrule 18 upon crimping of same. The valve housing 26 has a plurality of slots 38 which enable the interior 36 of the valve housing 26 to communicate with the interior 40 of the can body 16. The valve stem 22 has two channels 44, 46. Each channel, 44, 46 comprises a longitudinal passageway and a transverse passageway. The transverse passageway of the valve stem channel 44 is disposed so that, when the pressurised medicament container arrangement 14 is in its closed position as shown in FIG. 1, the metering chamber 30 is in communication with the interior 36 of the valve housing 26 and thus is also in communication with the interior 40 of the can body 16. As explained in more detail below, the volume of the metering chamber 30 corresponds to the volume of medicament containing fluid administered in a single dose. In the closed position shown in FIG. 1, the dose is wholly contained in the metering chamber 30 and cannot escape to the outside of the pressurised medicament container arrangement 14 owing to the action of the outer seal 34.

To release a dose of medicament containing fluid, the valve stem 22 is pushed against the biasing action of the spring 28 into the interior 36 of the valve housing 26 to an extent that the valve stem channel 44 no longer communicates with the metering chamber 30. The valve stem 22 is designed so that, in this dispensing position, the valve stem channel 46 of the valve stem 22 communicates with the metering chamber 30, thereby allowing the dose of medicament containing fluid in the metering chamber 30 to be dispensed through the valve stem 22. The dose then passes through the passageway 12e, the opening 12f and the open ended passage 12b to exit the device.

When the valve stem 22 is subsequently released the biasing action of the spring 28 causes the valve stem 22 to move back towards the position shown in FIG. 1. Thus, the valve stem channel 46 assumes a position whereby the metering chamber 30 is sealed against the outside, and the valve stem channel 44 assumes a position whereby the interior 36 of the valve housing 26 is in communication with the metering chamber 30. Owing to the pressure differential between the relatively high pressure interior 40 of the can body 16 and the relatively low pressure of the metering chamber 30, the metering chamber 30 is refilled with another dose of the medicament containing fluid.

The pressurised dispenser device 10 shown in FIG. 1 is one example of such a device, and many other metering arrangements are known which differ to a greater or lesser degree in their precise mode of action. The present invention does not lay claim to the mode of action of the device shown in FIG. 1 or of any other pressurised dispenser device. Rather, the present invention provides devices and components for same which are treated so as to inhibit losses of medicaments to internal surfaces of the device, and associated methods of production of such devices and components. The device shown in FIG. 1 is provided in order to assist the reader's appreciation of how the present invention might be applied. The skilled reader will appreciate that the present invention can be applied to other designs of pressurised dispenser device than the one shown in FIG. 1, and indeed can be applied to different types of medicament dispenser devices than pressurised dispenser devices.

The present invention provides methods of surface treatment which inhibit losses of the medicament to the internal surfaces of the pressurised dispensing device. The process utilises a surface modification of a metallic substrate in place of the prior art processes of directly coating the metallic substrate. However, the invention encompasses the deposition of a polymer coating onto the surface modified metallic substrate. A first embodiment of the invention will now be described with reference to a fluorination process, wherein the surface treatment produced metal fluoride moieties at the surface of a can body. Under correct plasma conditions, a fluorocarbon gaseous precursor can be completely broken down into its atomic constituents. Under appropriate control of process conditions such as pressure, power and residence time of the precursor gas, polymerisation does not occur and the surfaces subjected to the plasma are not coated. Instead, the surface is bombarded with fluorine and carbon atoms/ions. CF4 has been found to be the most suitable gaseous fluorocarbon precursor, and without wishing to be limited by any particular theory, it is believed that this is because the CF4 molecule provides the highest possible ratio of fluorine to carbon. Other suitable precursors include C2F6, C3F8, C4F8, CF5F10, HFA134a and HFA227.

Figure 2:
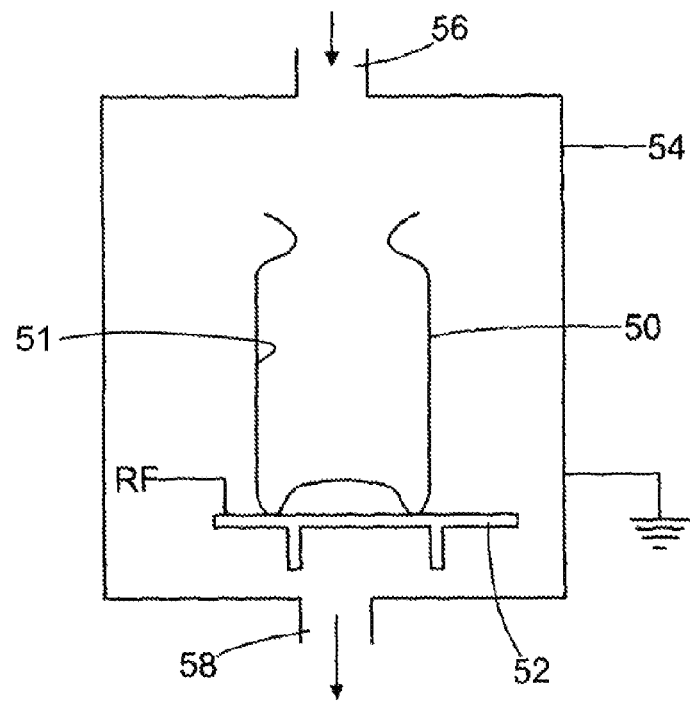
FIG. 2 shows a first embodiment of an arrangement for treating a can body.

FIG. 2 shows an arrangement in which a can body 50 is surface modified in accordance with the invention. In the arrangement, the can body 50 is maintained at RF potential by positioning the can 50 on a flat table 52 which is itself held at RF potential. The can 50 and table 52 are positioned inside a plasma reactor 54 which acts an earth electrode. The earth electrode can be the plasma chamber itself or an additional electrode. The plasma reactor 54 has a gas feed inlet 56 and an outlet 58 for exhausting gases. The plasma reactor 54 is connected to a suitable gas delivery source and a suitable exhaust system including a pumping arrangement. These additional items are not shown in FIG. 2, but suitable arrangements would readily suggest themselves to the skilled reader. The precursor fluorocarbon gas is delivered into the plasma reactor 54 through the gas feed inlet 56 from the delivery source which typically includes one or more mass flow controllers. Surface modification occurs when the gaseous fluorocarbon precursor is flowed into the plasma reactor 54, and a suitable plasma is produced. Typically 13.56 MHz RF power is applied to the can 50, and the plasma is struck using techniques well known in the art. Other RF frequencies might be used to equal effect, and it is anticipated that frequencies within the range of 4 kHz to 20 MHz might be utilised in a continuous or pulsed mode. During the process, fluorine (either neutral or ionised) reacts with the metal oxide surface layer of the can 50 and preferentially displaces oxygen, thereby forming a metal fluoride. In a preferred embodiment, the can is formed from aluminium, and before treatment has a surface layer of aluminium oxide, which is native or processed in. Surface modification in accordance with the invention provides a surface layer 51 of aluminium fluoride, which is extremely stable and provides a substrate which does not autocatalyse/degrade many drug formulations and is less susceptible itself to corrosion.

It is preferred to hold the can 50 at RF potential during the process, since an intense plasma can be developed. In particular, the RF electrode adopts a DC bias in forward power control. The level of this DC bias is proportional to the bombardment energy of incoming ions created in the plasma. If the DC bias exceeds about 350 volts, then the level of bombardment is significant, and fluorine ions are accelerated to an extent where they become readily embedded in the can surface, and carbon, native oxide, and other deleterious material can be sputtered away. The process is particularly efficient above 500 volts. It is particularly advantageous if the power supply to the can 50 is driven under DC bias control, i.e., the power is allowed to fluctuate whilst driving a constant high DC bias. In this way, the level of bombardment and treatment during the process is kept constant. A further advantage is observed when treating components such as the can body 50, in which the plasma is developed within a substantially enclosed area. In this case, a "hollow cathode" like effect is observed, and it has been found that electrons emitted at the RF potential of the can body 50 (which are driven by the DC bias) cannot escape the physical constraints of the can body 50. The effect is that the plasma created within the can body 50 is many times more energetic than that of the volume outside the can. This results in the surface being heavily bombarded with reactive fluorine at significantly lower power levels than might be expected, which has the effect that the process is more efficient. As representative but non-limiting examples of process conditions, the pressure in the plasma reactor may be in the range of $1 \times 10-2$ to 10 mbar, with a preferred range being $7 \times 10-2$ to $3 \times 10-1$ mbar. Power densities between 0.05 to 5 Wcm2 can be utilised. DC bias can be in the range of 100 to 800 volts, although, as mentioned above, a DC bias of greater than 350 volts is preferred. The DC bias is typically less than 700 volts, and advantageously is in the range of 400 to 550 volts. A plurality of can bodies may be positioned on the table 52 in order to provide a batch treatment process. The use of per-fluorocarbons is preferred, although the process will also work with hydrofluorocarbons, albeit with some compromise to the speed and/or effectiveness of the processing.

XPS has been used to characterise the fluorinated surface of aluminium can bodies which have been treated in this way. After pressing and washing, the surface of a can as received contains a high degree of oxide (typically 40 to 55 At % oxygen as measured by XPS) and 20 to 30 At % carbon from drawing oils or general adsorption from the atmosphere. After fluorination in accordance with the invention, a distinct chemical shift is observed from the aluminium oxide to a fluoride with about 5 At % oxygen, 45 At % fluorine as measured by XPS, with the remainder aluminium and its alloying elements. A second peak is observed in the XPS spectra of aluminium can bodies before treatment in accordance with the invention. Without wishing to be bound by any particular theory or conjecture, it is believed that the second peak corresponds to unreacted metal ions. Without treatment, it is believed that around 30 At % metal ions are present at the surface. After treatment, the unreacted metal ion content drops substantially, and it is possible to reduce the metal ion content to below 1 At %.

Figure 3:
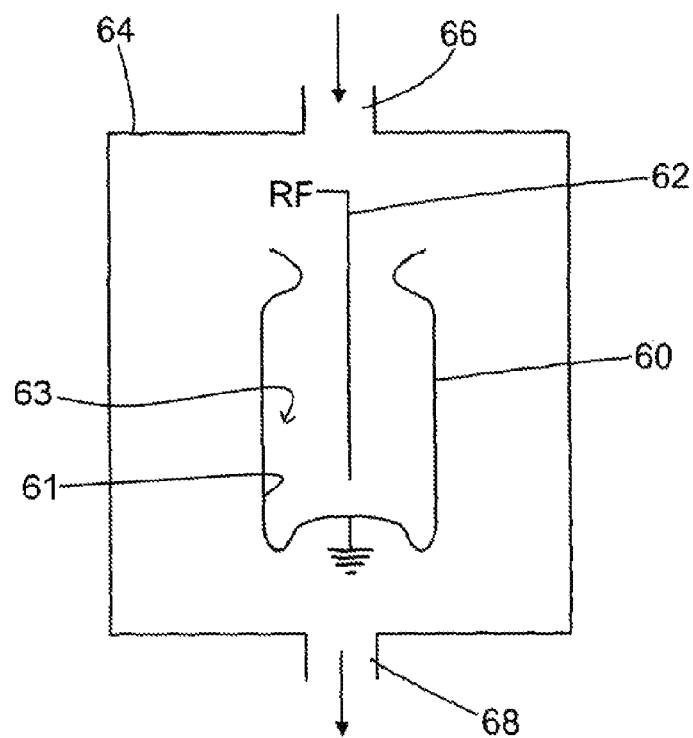
FIG. 3 shows a second embodiment of an arrangement for treating a can body.

FIG. 3 depicts a further embodiment in which surface modification is performed, and subsequently a polymer coating is deposited on a can body 60. In this embodiment, a can body 60 is earthed, and an elongate RF electrode 62 is disposed in the interior of the can body 60 substantially along the can body's longitudinal axis. The can body 60 resides in a plasma reactor 64 which has a gaseous precursor feed inlet 66 and an outlet 68 for exhausting gases. As with the embodiment shown in FIG. 2, an appropriate gas delivery source and exhaust system (not shown) would be used in conjunction with the arrangement shown in FIG. 3. The RF electrode 62 can be of any suitable form, such as a pin or like structure or coil. After any initial process steps such as cleaning (which is described in more detail below), the process precursor gas is introduced into the plasma reactor 64 under mass flow control. The pressure in the plasma reactor 64 is allowed to stabilise at process conditions, and is controlled via a suitable arrangement such as a throttle butterfly valve (not shown) on the exhaust outlet 68 or alternatively by gas flow using a mass flow controller. The power is supplied to the RF electrode 62, and a relatively intense plasma is created in order to provide the surface modification. The precursor gas may be a per-fluorocarbon in order to produce a fluorinated surface 61 having metal-fluorine moieties and a subsequent fluorocarbon polymer coating 63, or may be a hydrocarbon precursor which is used to provide a modified surface having metal-carbide moieties and a subsequent hydrocarbon polymer coating. The coating can be any polymerised layer. Under representative process conditions, the oxygen content in the interior surface of the can body 60 is seen to drop from 40 to 44 At % to 5 to 10 At % as measured by XPS within two minutes of the commencement of processing. For the remainder of the process, the power supply is switched to or maintained in DC bias mode, and the modified surface is coated with a plasma polymerized layer. The plasma polymerised layer may instead be deposited using forward power mode. With the configuration shown in FIG. 3, with the RF electrode 62 positioned in the earthed can body 60, the effective electrical resistance of the can increases as the can gets progressively coated. As a result, the normal electron path to the earthed can is reduced as the coating thickness increases. Forward power operation is typically used in prior art plasma polymerization processes for coating components, such as can bodies, for medicament dispenser devices. However, under normal forward power operation, electron emission from the power supply will be reduced as the processing proceeds, self DC bias will be reduced, and plasma intensity will drop, resulting in a weak porous coating in its latter stages. In contrast, by operating a DC bias control for a significant proportion or all of the coating cycle, the DC bias is fixed, and a constant electron emission is maintained which in turn maintains a constant plasma density. This provides a constant deposition rate, and a high quality, uniform coating, both in terms of the lateral extent of the coating, and in terms of the depth of coating. This steady rate of coating can be maintained until a desired thickness is obtained. Typically the desired thickness is in the range of 15 to 200 nm, but the invention is not limited in this regard. During polymerisation, the DC bias is preferably in the range of 50 to 500V, most preferably 50 to 350V. A further advantage of DC bias control of the plasma polymerisation of a coating is encountered at the end of the process. It is typical in the prior art for coated components to be stored for between one and seven days so that reactive surface sites on the coating are allowed to saturate. In the process described in relation to FIG. 3, the power supply and DC bias mode can be simply switched off, and the supply of the gaseous monomer is permitted to flow for a period thereafter, which is typically in the range of 5 seconds to 10 minutes, with a preferred range of 30 seconds to 1 minute. The intensity of the plasma drops off gradually as electrons in the capacitive reservoir are used up, allowing the surface to be flushed with a plasma containing relatively fewer ionised species, until the surface is flushed with "neat," unionised monomer. The effect is to "cap off" the coating with unreactive species and monomer which enables the coated component to be retrieved from the plasma reactor 64 without a subsequent rest period being required.

The configuration shown in FIG. 3 wherein the component to be treated is earthed and a separate RF electrode is used, is a preferred configuration for plasma polymerising a polymer coating. The configuration is also suitable for the earlier surface modification step. The advantage of using the same configuration for both the surface modification step and the subsequent plasma polymerisation step is that the two steps can be performed as part of one continuous operation. It is particularly advantageous as gas/monomer can be used both as the precursor to the surface modification step, and also as a monomer gas for the plasma coating step. When the surface of the component is converted to metal-fluoride moieties, it is preferred that the precursors/monomers are one of CF4, C2F6, C3F8, C4F8, HFA134a or HFA224. Where it is intended that modification of the components surface produces a metal carbide layer, it is preferred that the precursor/monomer is methane or ethane, but other Alkanes, Alkenes and Alkynes up to C5 might be used.

The component treated by the present invention may be subjected to a pre-cleaning step prior to the surface modification step. It is common in the prior art to use a pre-cleaning step which utilises oxygen. The present inventors have realised that the use of oxygen in the pre-cleaning step, or indeed elsewhere in the processing of the component, is highly disadvantageous. The present inventors have found that the presence of oxygen is detrimental to the build up of polymer coatings and to their adhesion. Oxygen absorbed into e.g. the walls of the plasma reactor and other parts can leach out to dissociate the coating and/or the monomer, which is deleterious to the polymer and increases processing time. Any pre-cleaning step should therefore exclude oxygen. A particularly useful pre-cleaning step uses an argon plasma to clean the component prior to the surface modification step.

The invention claimed is:

1. A medicament dispenser device, the device including at least one metallic component having at least one non-metallic surface which comes into contact with a medicament during storage or use of the device, in which said non-metallic surface has an interface with the underlying metallic component which substantially comprises metal-fluoride and/or metal carbide moieties, and the interface comprises less than about 15 At % oxygen as measured by XPS.

2. The medicament dispenser device according to claim 1 in which the non-metallic surface consists essentially of the interface so that the interface comes into contact with the medicament during storage or use of the device.

3. The medicament dispenser device according to claim 1 in which the non-metallic surface includes a coating which is deposited onto the interface so that the coating comes into contact with the medicament during storage or use of the device.

4. The medicament dispenser device according to claim 3 in which the coating is a polymer coating or an inorganic coating.

5. The medicament dispenser device according to claim 4 in which the coating is a plasma polymerised polymer coating.

6. The medicament dispenser device according to claim 4 in which the interface substantially comprises metal-fluoride moieties, and the polymer coating is a fluorocarbon polymer.

7. The medicament dispenser device according to claim 4 or in which the interface substantially comprises metal-carbide moieties, and the polymer coating is a hydrocarbon polymer.

8. The medicament dispenser device according to claim 1 in which the interface comprises less than about 5 At % oxygen as measured by XPS.

9. The medicament dispenser device according to claim 1 in the form of a pressurised dispenser device which dispenses the medicament in a carrier fluid.

10. The medicament dispenser device according to claim 1 including a metallic can body, in which the non-metallic surface is an interior surface of the can body.

11. The medicament dispenser device according to claim 1 in which the metallic component is formed from aluminium.

12. The medicament dispenser device according to claim 1 in which the interface comprises less than about 10 At % oxygen as measured by XPS.

* * * * *